US012584086B2

(12) United States Patent
Cirit

(10) Patent No.: US 12,584,086 B2
(45) Date of Patent: Mar. 24, 2026

(54) MICROFLUIDIC DEVICES AND METHODS OF DESIGNING AND USING MICROFLUIDIC DEVICES

(71) Applicant: Javelin Biotech, Inc., Woburn, MA (US)

(72) Inventor: Murat Cirit, Cambridge, MA (US)

(73) Assignee: Javelin Biotech, Inc., Woburn, MA (US)

( * ) Notice: Subject to any disclaimer, the term of this patent is extended or adjusted under 35 U.S.C. 154(b) by 673 days.

(21) Appl. No.: 16/834,235

(22) Filed: Mar. 30, 2020

(65) Prior Publication Data

US 2021/0301238 A1 Sep. 30, 2021

(51) Int. Cl.
| | |
|---|---|
| C12N 5/077 | (2010.01) |
| C12M 1/00 | (2006.01) |
| C12M 3/06 | (2006.01) |
| C12N 5/071 | (2010.01) |

(52) U.S. Cl.
CPC ............ C12M 23/16 (2013.01); C12M 29/10 (2013.01); *C12N 5/0653* (2013.01); *C12N 5/0658* (2013.01); *C12N 5/0686* (2013.01)

(58) Field of Classification Search
None
See application file for complete search history.

(56) References Cited

U.S. PATENT DOCUMENTS

| | | | |
|---|---|---|---|
| 8,318,479 B2 | 11/2012 | Domansky et al. | |
| 2008/0064088 A1 * | 3/2008 | Shuler .................... | C12M 23/16 |
| | | | 435/293.1 |
| 2017/0227525 A1 | 8/2017 | Griffith et al. | |
| 2019/0032021 A1 | 1/2019 | Ingber et al. | |

FOREIGN PATENT DOCUMENTS

| | | | | |
|---|---|---|---|---|
| AU | 2011287881 | 7/2014 | | |
| JP | 2011-528232 A | 11/2011 | | |
| JP | 2016-535591 A | 11/2016 | | |
| WO | WO 2003/027223 | 4/2003 | | |
| WO | WO-03027223 A2 * | 4/2003 | ............ | C12M 21/08 |
| WO | WO 2011/014674 | 2/2011 | | |
| WO | WO 2013/086329 | 6/2013 | | |
| WO | WO 2014/120772 | 8/2014 | | |
| WO | WO 2019/122291 | 6/2019 | | |
| WO | WO 2019/163825 A1 | 8/2019 | | |

OTHER PUBLICATIONS

Young et al. "Monitoring of microphysiological systems: integrating sensors and real-time data analysis toward autonomous decision-making." ACS sensors 4.6 (2019): 1454-1464. (Year: 2019).*

Edington et al. "Interconnected microphysiological systems for quantitative biology and pharmacology studies." Scientific reports 8.1 (2018): 1-18. Published online Mar. 14, 2018 Supplemental Contents (Year: 2018).*

Taylor et al. "Harnessing human microphysiology systems as key experimental models for quantitative systems pharmacology." Concepts and Principles of Pharmacology: 100 Years of the Handbook of Experimental Pharmacology (2019): 327-367. (Year: 2019).*

Low et al. "Tissue chips—innovative tools for drug development and disease modeling." Lab on a Chip 17.18 (2017): 3026-3036. (Year: 2017).*

International Invitation to Pay Additional Fees and, Where Applicable, Protest Fee in International Appln. No. PCT/US2021/24899, dated Jun. 24, 2021, 3 pages.

International Search Report and Written Opinion in International Appln. No. PCT/US2021/24899, dated Sep. 27, 2021, 12 pages.

Cirit, Murat, and Cynthia L. Stokes. "Maximizing the Impact of Microphysiological Systems with in Vitro-in Vivo Translation." Lab on a Chip, vol. 18, No. 13, Jun. 26, 2018, pp. 1831-1837.

Edington, Collin D. et al. "Interconnected Microphysiological Systems for Quantitative Biology and Pharmacology Studies". Scientific Reports, vol. 8, No. 4530, Mar. 14, 2018, pp. 1-18.

Maass, Christian, et al. "Multi-Functional Scaling Methodology for Translational Pharmacokinetic and Pharmacodynamic Applications Using Integrated Microphysiological Systems (MPS)." Integrative Biology (Camb), vol. 9, No. 4, Apr. 18, 2017, pp. 290-302.

Maass, Christian, et al. "Translational Assessment of Drug-Induced Proximal Tubule Injury Using a Kidney Microphysiological System." CPT: Pharmacometrics Syst. Pharmacol, vol. 8, Sep. 2019, pp. 316-325.

Stokes, CL, et al. "Physiome-on-a-Chip: The Challenge of 'Scaling' in Design, Operation, and Translation of Microphysiological Systems." CPT: Pharmacometrics Syst. Pharmacol., vol. 4, Oct. 10, 2015, pp. 559-562.

Tsamandouras, Nikolaos, et al. "Integrated Gut and Liver Microphysiological Systems for Quantitative In Vitro Pharmacokinetic Studies." AAPS Journal, vol. 19, No. 5, 27 Sep. 2017, pp. 1499-1512.

Extended European Search Report in European Appln. No. 21780619.9, mailed on Sep. 21, 2023, 7 pages.

* cited by examiner

Primary Examiner — Emily A Cordas
(74) Attorney, Agent, or Firm — Fish & Richardson P.C.

(57) ABSTRACT

Microfluidic platforms including multiple microphysiological systems. At least one of the platforms include: at least one inlet; a plurality of organ constructs, each organ construct of the plurality of organ constructs being sized relative to other organ constructs of the plurality of organ constructs based on at least one predetermined human pharmacokinetic (PK) parameter; and a plurality of channels, each channel of the plurality of channels causing an organ construct of the plurality of organ constructs to be in fluidic communication with at least one other organ construct of the plurality of organ constructs.

17 Claims, 10 Drawing Sheets

Analyze Interaction Between Molecular Compound and Plurality of Organ Constructs (210)

Determine Plurality of Concentration Profiles (220)

Determine at Least One PK Parameter (230)

Determine at Least One Design Parameter (240)

Design Multi-MPS Platform (250)

In vitro drug profiles

Curve fitting $$\frac{d[C]}{dt} = -k[C]$$

d[C] – drug concentration
k – elimination rate constant
V – volume

CL = k / V

In vitro drug profiles

Concentration

Insert Molecular Compound Into Microfluidic Device
(710)

Cause Molecular Compound to Interact with Plurality of Organ Constructs
(720)

Determine Plurality of Concentration Profiles
(730)

Determine Plurality of First PK Parameters
(740)

Translate Plurality of First PK Parameters to Plurality of Second PK Parameters
(750)

MICROFLUIDIC DEVICES AND METHODS OF DESIGNING AND USING MICROFLUIDIC DEVICES

FIELD OF THE INVENTION

This disclosure generally relates to microfluidic devices.

BACKGROUND

A microphysiological system (MIPS) includes an interconnected set of two- or three-dimensional cellular constructs that are frequently referred to as organs-on-chips, tissue chips, or in vitro organ constructs. The constructs are typically made with immortalized cell lines, primary cells from animals or humans, or organ-specific cells derived from naïve cells, human embryonic stem cells, and induced pluripotent stem cells (iPSCs). Individually, each construct can be designed to recapitulate the structure and function of a human organ or organ region, paying particular attention to the cellular microenvironment and cellular heterogeneity. When coupled together to create an MPS, these constructs offer the possibility of providing, in vitro, an unprecedented physiological accuracy for the study of cell-cell, drug-cell, drug-drug, and organ-drug interactions, if drug delivery can be properly modeled.

Pharmacokinetics (PK) is a branch of pharmacology dedicated to determining the fate of substances administered to a living organism. Typically, the substances of interest can include any chemical xenobiotic such as: pharmaceutical drugs, pesticides, food additives, cosmetics, and so forth. In some cases, PK attempts to analyze chemical metabolism, absorption, metabolism, biodistribution, and/or excretion, and attempts to discover the fate of a chemical from the moment that it is administered up to the point at which it is eliminated from the body. In general, PK studies can give insight as to how an organism processes a drug.

Pharmacodynamics (PD) refers to the study of the biochemical and physiologic effects of drugs (for example, pharmaceutical drugs). The effects can include those manifested within animals (including humans), microorganisms, or combinations of organisms (for example, infection). Pharmacodynamics places particular emphasis on dose-response relationships, that is, the relationships between drug concentration and effect. Generally, PD studies can give insight as to how a drug affects an one or more diseases in an organism.

PK/PD modeling is a technique that combines the two classical pharmacologic disciplines of pharmacokinetics and pharmacodynamics. It integrates a pharmacokinetics and a pharmacodynamics model component into one set of mathematical expressions that allows the description of the time course of effect intensity in response to administration of a drug dose.

SUMMARY

In at least one aspect of the present disclosure, a method is provided. The method includes analyzing an interaction between a molecular compound and each organ construct of a plurality of organ constructs, each organ construct of the plurality of organ constructs corresponding to an organ type of a plurality of organ types. The method includes determining, based on the analysis, a plurality of concentration profiles, each concentration profile of the plurality of concentration profiles corresponding to an organ construct of the plurality of organ constructs. The method includes determining, for each organ type of the plurality of organ types and based on the concentration profiles, at least one pharmacokinetic (PK) parameter. The method includes determining, based on the at least one PK parameter, at least one design parameter. The method includes designing a multi-organ construct platform based on the at least one design parameter.

Determining at least one design parameter can include determining a relative size pattern between the plurality of organ constructs based on at least one predetermined human PK parameter. Analyzing an interaction can include determining, for each organ construct of a plurality of organ constructs, at least one predesign parameter of that organ construct, in which the at least one predesign parameter is determined based on a desired application of the plurality of organ constructs.

The plurality of organ constructs can include at least one of: a gastrointestinal tract organ construct, a liver organ construct, a kidney organ construct, a muscle organ construct, or an adipose organ construct. The molecular compound can include a xenobiotic and the plurality of concentration profiles can include a plurality of xenobiotic concentration profiles.

Determining at least one PK parameter can include analyzing the plurality of concentration profiles using at least one ordinary differential equations. The at least one PK parameter can include at least one of: a clearance, a permeability, and a volume of distribution.

The at least one design parameter can include at least one of: a volume of at least one organ construct, a surface area of at least one organ construct, a number of cells of at least one organ construct, an arrangement of cells of at least one organ construct, a flow pattern, a volume of at least one channel, a flow rate, and a flow partitioning value. The designed multi-organ construct platform can include four or more organ constructs.

In an aspect, a system is provided. The system includes at least one inlet. The system includes a plurality of organ constructs, each organ construct of the plurality of organ constructs being sized relative to other organ constructs of the plurality of organ constructs based on at least one predetermined human pharmacokinetic (PK) parameter. The system includes a plurality of channels, each channel of the plurality of channels causing an organ construct of the plurality of organ constructs to be in fluidic communication with at least one other organ construct of the plurality of organ constructs.

The plurality of channels can be configured to cause a molecular compound to flow through the system at a circulation flow rate at which the molecular compound is distributed at a threshold distribution rate. The plurality of organ constructs can include at least one gastrointestinal tract organ construct, at least one liver organ construct, at least one kidney organ construct, and at least one of a muscle organ construct or an adipose organ construct. The least one organ construct of the plurality of organ constructs can include two membrane compartments separated by a porous membrane. The plurality of organ constructs can include at least four organ constructs. The plurality of organ constructs can include at least one of: a gastrointestinal tract organ construct, a liver organ construct, a kidney organ construct, a muscle organ construct, or an adipose organ construct. Each of the plurality of organ constructs can include at least one of: an apical compartment and a basolateral compartment.

At least a portion of the plurality of channels can be configured to cause a fluid to continuously circulate between at least a portion of the plurality of organ constructs. The system can further include at least one second channel in fluidic communication with at least one organ construct of the plurality of organ constructs and configured to facilitate fluidic flow through the at least one organ construct. The plurality of organ constructs can include a gastrointestinal tract organ construct and a kidney organ construct. The at least one inlet can include a first inlet in fluidic communication with the gastrointestinal tract organ construct and a second inlet in fluidic communication at least one of the plurality of channels.

In an aspect, a method is provided. The method includes inserting a molecular compound into a microfluidic device comprising a plurality of organ constructs. The method includes flowing the molecular compound through the microfluidic device to cause the molecular compound to interact with the plurality of organ constructs. The method includes determining, based at least partially on the interacting, a plurality of concentration profiles. The method includes determining, based at least partially on the plurality of concentration profiles, a plurality of first pharmacokinetic (PK) parameters including a first type. The method includes translating the plurality of first PK parameters to a plurality of second PK parameters including a second type.

Flowing the molecular compound through the microfluidic device can include causing distribution of the molecular compound at a circulation flow rate at which the molecular compound is distributed as a threshold distribution rate.

The plurality of organ constructs can include at least four organ constructs. The plurality of organ constructs can include at least one of: a gastrointestinal tract organ construct, a liver organ construct, a kidney organ construct, a muscle organ construct, or an adipose organ construct. The plurality of organ constructs can include at least one gastrointestinal tract organ construct, at least one liver organ construct, at least one kidney organ construct, and at least one of a muscle organ construct or an adipose organ construct. Each of the plurality of organ constructs can include at least one of: an apical compartment or a basolateral compartment.

The at least one pharmacokinetic parameter can include at least one of: a clearance, a permeability, or a volume of distribution. Determining at least one pharmacokinetic parameter can include using at least one ordinary differential equation. The first type of PK parameters can include in vitro PK parameters and the second type of PK parameters can include human PK parameters.

These and other aspects, features, and implementations can be expressed as methods, apparatus, systems, components, program products, means or steps for performing a function, and in other ways.

These and other aspects, features, and implementations will become apparent from the following descriptions, including the claims.

Implementations of the present disclosure can provide one or more of the following advantages. When compared with conventional techniques, implementations of the systems described in this disclosure can: be designed to better replicate in vivo (e.g., human) biological systems enable the study of organ-specific contribution to pharmacokinetics; incorporate organ-to-organ crosstalk; provide enough media volume for frequent sampling to determine PK profiles; facilitate recirculation of media to enable the study of PK associated with both drugs that are cleared slow and drugs that are cleared quickly; enable PK studies while each organ construct is simultaneously contributing to the PK profile; be scaled based on individual MPS function relevant to PK; and incorporate proper mechanical cues, such as shear stress on gut and kidney organ constructs. When compared with conventional techniques, implementations of the systems and methods described in this disclosure can: provide in vitro results that are more accurately translated to predicted in vivo results; facilitate designing MPS platforms that are optimized for a specific function; and provide faster PK analysis.

DETAILED DESCRIPTION

Figure 1:
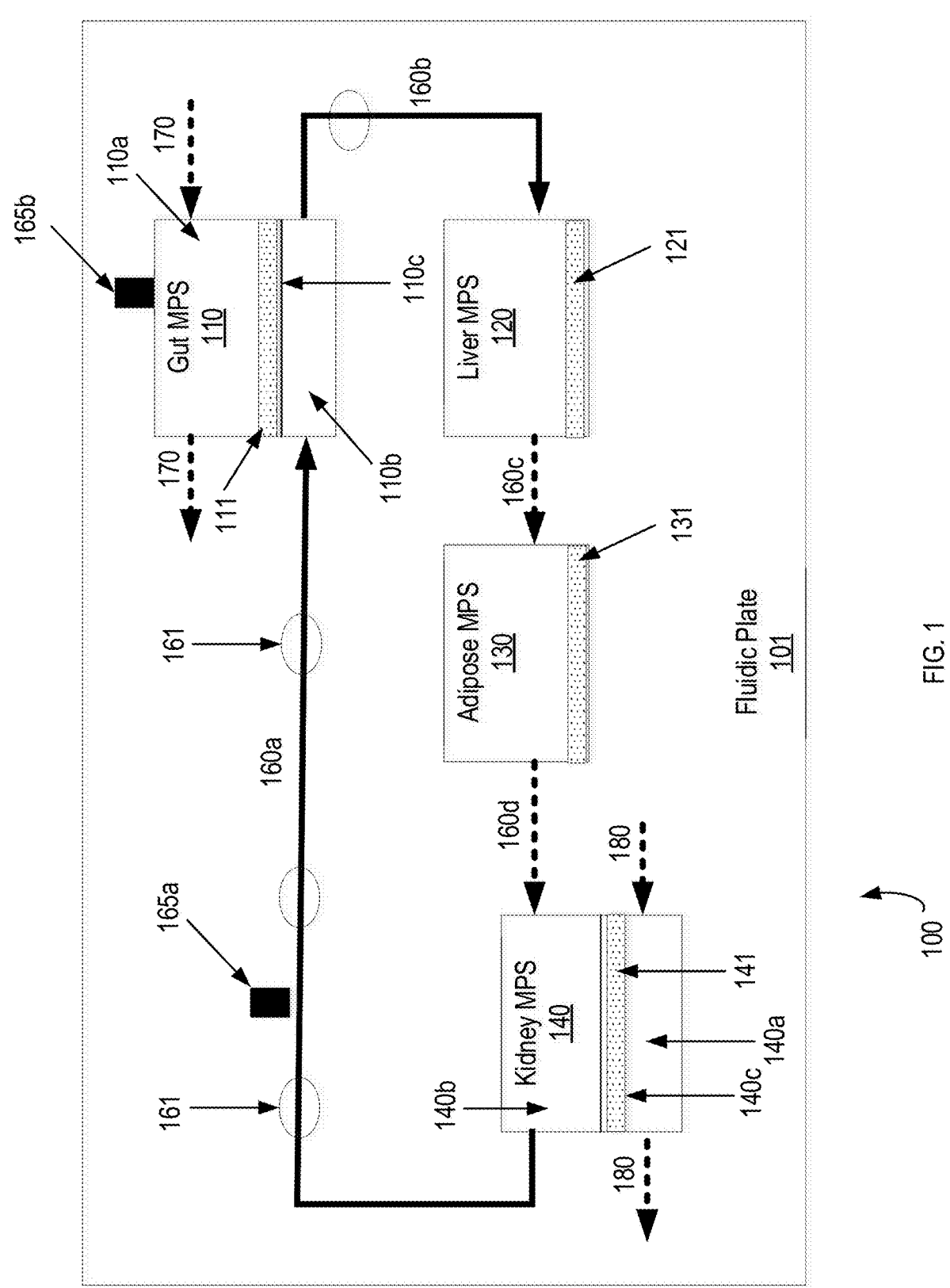
FIG. 1 is a block diagram illustrating an example multi-MPS platform.

Investigation of the PK properties of a drug can be particularly important during pre-clinical drug development, as it may facilitate decision-making regarding the dosage regimen in early-phase clinical studies. Animal species are often used to study the PK of a compound under development; however, such studies can be costly, can be considered unethical, and often fail to accurately capture the human phenotype. In vitro systems can be developed and employed to investigate the absorption, distribution, metabolism, and excretion (ADME) of a compound. Although these systems have been extremely valuable in drug development, they are not without limitations and the need for more physiologically realistic and better predictive in vitro models is widely recognized.

MPSs (sometimes referred to as organ constructs and organ-on-chips (OOC) in this specification) can provide numerous benefits to pre-clinical drug development. The term MPSs can encompass a range of compositionally complex (for example, more than one cell type) and three dimensional (3D) cell cultures that are dynamically perfused, thus capturing more features of human organ or tissue function compared to the traditional static 2D cell cultures. Additionally, the use of micro-machined biomimetic reactor platforms can facilitate in vitro re-creation of the mechanical, fluidic, spatial, and chemical stimuli and cues that a tissue may be exposed to in vivo. To better recapitulate human physiology at a systemic level and establish better pharmacologic pre-clinical models that translate more accurately to human outcomes, multi-MPS platforms can be designed to interconnect several MPSs representing facets of different organs together and thus allow organ-organ inter-action and cross-signaling. In many cases, single MPS and multiple MPS platforms can be designed to mimic specific organ functions, microarchitecture, and organ-organ cross-talk relevant to a biological question of interest.

MPSs have the potential to offer means for exploring the PK properties of a drug pre-clinically. For such investiga-tions, the integration of gut and liver MPSs may be impor-tant as these two organs can play a central role on the biodistribution and bioavailability of an orally administrated compound (through processes such as intestinal permeabil-ity and hepatic metabolism). However, conventional MPS technology can have one or more of the following limita-tions with respect to their application for PK studies: (1) they employ materials (for example, Polydimethylsiloxane (PDMS)) that non-specifically adsorb lipophilic compounds; (2) they use relatively low culture volumes and cell numbers that can negatively affect the output biological signal and the collection of high-content measurements; (3) they do not allow continuous access to the MPS compartments for direct and frequent sampling of circulating drugs/metabolites, and thus data-rich quantitative PK profiles across all platform compartments cannot always be obtained; and (4) they are usually not coupled with a mathematical modeling method-ology to disentangle the biology-related parameters (for example, intestinal permeability, intrinsic hepatic clearance, and so forth) from system-specific processes and parameters (for example, flow rates, surface areas), a step which can be important for subsequent in vitro to in vivo translation.

The systems and methods described in this specification can be used to provide a solution to the previously men-tioned disadvantages. In some implementations, a method of designing a multiple-MPS platform is described. The method can include physically designing several individual MPSs, causing a drug to interact with each MPS to generate a concentration profile for each MPS, using the concentra-tion profiles to estimate a plurality of PK parameters (for example, coefficients related to gut permeability, hepatic clearance, renal excretion, volume of distribution, and so on) independently of the design specifications of the individual MPSs, using the PK parameters to determine design param-eters for a multi-MPS platform, and designing a multi-MPS platform using the design parameters. The method can facilitate optimizing the multi-MPS platform such that each MPS of the platform are designed relative to each other to replicate known in-human PK profiles. The resulting MPS platform can also include channels that connect each MPS with at least one other MPS to facilitate a continuous circulated flow of a drug between the MPSs. The method can design each channel to facilitate flow rates, flow patterns, and flow partitioning such that the platform, as a whole, is optimized to replicate known in-human PK profiles. In some implementations, the resulting MPS platform includes single pass flow channels that facilitate the application of fluid shear stress to at least some of the MPSs. The applications of fluid shear stress to an MPS can stimulate cellular responses that can be important for, as an example, endothe-lial cell function and are atheroprotective, and can facilitate differentiation of cells during cell culturing.

In some implementations, a method of performing PK analysis using a multi-MPS platform is described. The method can include causing a drug to flow through the platform to cause the drug to interact with each of the MPSs of the MPS platform. Samples of the MPSs are collected at several time points and, for each sample, the drug can be quantified using, for example, mass spectrometry. Based on the drug quantification, in-vitro PK profiles (concentration/ time) can be generated. Based on these PK profiles, in-vitro PK parameters (for example, clearance, permeability, and so forth) can be determined. The in-vitro PK parameters can be translated to human PK parameters using computational modeling and, in some implementations, machine learning.

In the following description, for the purposes of expla-nation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscur-ing the present disclosure.

In the drawings, specific arrangements or orderings of schematic elements, such as those representing devices, modules, instruction blocks and data elements, are shown for ease of description. However, it should be understood by those skilled in the art that the specific ordering or arrange-ment of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described in this specification. Although headings are provided, data related to a particular heading, but not found in the section having that heading, may also be found elsewhere in this description.

FIG. 1 is a block diagram illustrating an example multi-MPS platform 100. The platform 100 includes a fluidic plate 101. In some implementations, the fluidic plate 101 is at least partially constructed from polysulfone plastic, which can help minimize drug adsorption during use of the platform 100. In some implementations, the fluidic plate 101 is at least partially constructed from one or more of polystyrene, polycarbonate, and cyclic olefin copolymer. The fluidic plate 101 includes a plurality of MPSs 110-140. In the illustrated implementations, the plurality of MPSs 110-140 include a gut MPS 110, a liver MPS 120, an adipose MPS 130, and a kidney MPS 140. Although certain organ constructs are described with respect to the illustrated implementation, other organ constructs can be used in some implementations. In some implementations, the plurality of MPSs include one or more muscle MPSs and/or one or more skin MPSs in addition to the described MPSs of the illustrated implementation or alternative to one or more of the described MPSs of the illustrated implementation. Each of the plurality of MPSs 110-140 can be releasably attached to the fluidic plate 101 (for example, using transwell techniques) or integrated with the fluidic plate 101.

Each of the plurality of MPSs 110-140 can include a number of cells (that is, a number of cells and cell types) specific to an organ corresponding to that MPS. In some implementations, the gut MPS 110 corresponds to the esophagus, stomach, and/or pancreas, and includes one or more cells 111 (that is, cells and cell types) typically found in such organs, such as Caco2-BBe epithelial cells, mucin-producing goblet cells (HT29-MTX), primary monocyte-derived dendritic cells, and so forth. In some implementations, the liver MPS 120 corresponds to the liver and includes one or more cells 121 typically found in the liver, such as hepatocytes, fibroblasts, kupffer cells, liver sinusoidal endothelial cells (LSECs), hepatic stellate cells, stroma, and so forth. In some implementations, the adipose MPS 130 corresponds to the adipose organ and includes one or more cells 131 typically found in the adipose organ, such as adipocytes. In some implementations, the Kidney MPS 140 corresponds to the kidney organ and includes one or more cells 141 typically found in the kidney, such as kidney glomerulus parietal cells, glomerulus podocytes, kidney proximal tubule brush border cells, collecting duct intercalated cells, and so forth.

In some implementations, one or more of the plurality of MPSs 110-140 include two or more compartments separated by a porous membrane. In the illustrated implementation, the gut MPS 110 includes an apical compartment 110a and a basolateral compartment 110b that are separated by a porous membrane 110c. The compartments 110a, 110b can approximate the absorption and filtering functions, for example, epithelial cells. As will be described later, a molecular compound (for example, a buffer including a drug) can be added to the gut MPS 110 through the apical compartment 110a, in which it interacts with the one or more cells 110 (for example, epithelial cells), which can be attached to the porous membrane 111, and then at least a portion of the molecular compound can be absorbed in the basolateral compartment 110b and flow out of the gut MPS 110 to begin circulation through the platform 110. In some implementations, the apical compartment 110a includes epithelial cells, and the basolateral compartment 110b includes immunity cells (for example, macrophages). Also, in the illustrated implementation, the kidney MPS 140 includes an apical compartment 140a and a basolateral compartment 140b separated by a porous membrane 140c. These compartments 140a, 140b can be configured to replicate the clearance function of the kidney organ. The basolateral compartment 140b can receive the molecular compound as it circulates through the platform 100, and at least a portion of the molecular compound (and media) can move through the porous membrane 140c while interacting with the one or more cells 141, which can be attached to the porous membrane 140c in the apical compartment 140a.

The fluidic plate 101 includes a plurality of channels 160a-d. Each of the channels 160a-d are configured to cause each of the plurality of MPSs 110-140 to be in fluidic communication with at least one other MPS of the plurality of MPSs 110-140. In the illustrated example, a first channel 160a provides fluidic communication between the kidney MPS 140 and the gut MPS 110, a second channel 160b provides fluidic communication between the Gut MPS 110 and the liver MPS 120, a third channel 160c provides fluidic communication between the liver MPS 120 and the adipose MPS 130, and a fourth channel 160d provides fluidic communication between the adipose MPS 130 and the kidney MPS 140. Each of the plurality of channels 160a-160d can include one or more pumps 161 to facilitate flow through the channels 160a-160d and MPSs 110-140.

As shown, the plurality of channels 160a-d are designed to provide a circular flow of a molecular compound in a media or buffer (for example, a drug in a media or buffer) between the MPSs of the plurality of MPSs 110-140. In some implementations, the plurality of channels 160a-d are designed to cause the drug to flow between the MPSs of the plurality of MPSs 110-140 at a predetermined system level flow rate. In some implementations, a system level flow rate describes a rate at which a portion of a drug sample flows from the gut MPS 110, to the rest of the MPSs 120-140, and back to the gut MPS 110. In some implementations, each of the plurality of channels 160a-d are individually designed to have different flow rates which, in combination, equal the system level flow rate. That is, the first channel 160a can cause a media or buffer (with or without a drug) to flow between the kidney MPS 140 to the gut MPS 110 at a first flow rate, while the second channel 160b can cause the drug sample to flow between the gut MPS 110 and the liver MPS 120 at a second flow rate that is different than the first flow rate.

In some implementations, the fluidic plate 101 includes single pass channels 170, 180 to cause fluids to flow through one or more of the plurality of MPSs 110-140 in a non-circulatory mannerIn the illustrated implementation, the fluidic plate 101 includes a first single pass channel 170 to cause fluids to flow through the gut MPS 110 and a second single pass channel 180 to cause fluids to flow through the kidney MPS 140. The single pass channels 170, 180 can facilitate apply fluid shear stress to the cells of the MPS, which can be helpful in stimulating cellular responses that can be important for, as an example, endothelial cell function and are atheroprotective, and cellular differentiation during cell maturation. Although described as non-circulatory in the illustrated implementation, in some implementations, one or more of the channels 170, 180 can be configured to cause fluids to flow through one or more of the plurality of MPSs 110-140 in a circulatory manner.

The fluidic plate 101 includes one or more inlets 165a, 165b. In the illustrated implementation, the fluidic plate 101 includes a first inlet 165a configured to receive a fluidic sample (such as a drug sample) and allow the fluidic sample to begin flowing through the platform 100 at a location of the first channel 160a. Insertion of the fluidic sample through the first inlet 165a can replicate intravenous (IV) dosing of a drug. The fluidic plate 101 also includes a second inlet 165b configured to receive a fluidic sample and allow the fluidic sample to begin flowing through the platform 100 at the gut MPS 110. Insertion of the fluidic sample through the second inlet 165b can replicate oral dosing of a drug. Although the first inlet 165a is illustrated as being between the kidney MPS 140 and the gut MPS 110, and the second inlet 165*b* is illustrated as being located on the gut MPS 110, other implementations are not so limited. In some implementations, the first inlet 165*a* is located between the liver MPS 120 and the adipose MPS 130. Such implementations can facilitate distinguishing between on-chip PK profiles of different types of drugs (for example, fast clearing and slow clearing drugs, fast permeable and slow permeable drugs, and so forth).

In constructing the platform 100, each of the plurality of channels 160*a*-160*d* and the plurality of MPSs 110-140 can be designed relative to each other to maximize some desired function (for example, performing PK analysis). In some implementations, each of the plurality of channels 160*a*-160*d* and the plurality of MPSs 110-140 are designed according to one or more design parameters (for example, media volume, number of cells by type, surface area, system level flow rate, flow pattern, flow partitioning, and so forth) to maximize the platform's 100 ability to approximate PK profiles in humans. Determining the one or more design parameters to maximize a desired functions is discussed later in this specification.

In some implementations, to operate the platform 100, the platform is coupled with a pneumatic plate, in which a pneumatic membrane can be used to separate the platform 100 from the pneumatic plate. The pneumatic plate can include a plurality of outlets configured to distribute compressed air to small ports below each of the pumps 161 of the platform 100. The distribution of compressed air can cause the pumps 161 to actuate, which can cause a fluidic sample to flow through the platform 100.

Figure 2:
FIG. 2 is a flow chart illustrating an example method of designing a multi-MPS platform.
Figure 2:
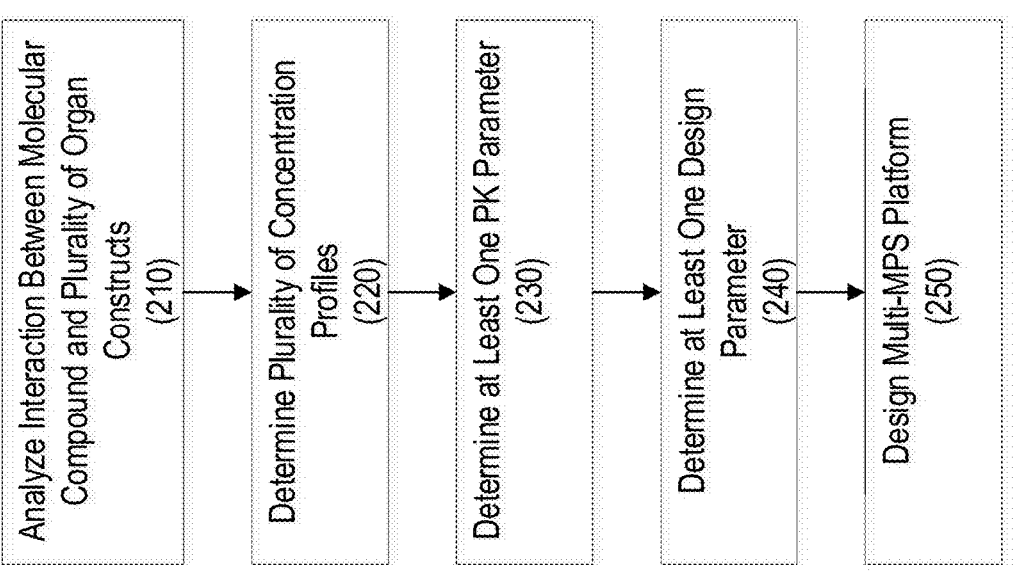

FIG. 2 is a flow chart illustrating an example method 200 of designing a multi-MPS platform. In some implementations, the method 200 is used to design the MPS platform 100 described previously with reference to FIG. 1. The method includes analyzing an interaction between a molecular compound and a plurality of organ constructs (block 210), determining a plurality of concentration profiles (block 220), determining at least one PK parameter (block 230), determining at least one design parameter (block 240), and designing a multi-MPS platform (block 250).

At block 210, a plurality of MPSs are designed, in which each of the MPSs correspond to a particular organ (for example, liver, adipose, skin, muscle, gut, kidney, and so forth). A drug sample is caused to interact with each of the MPSs for a predetermined amount of time by, in some implementations, flowing the drug sample through the MPSs. Pre-design parameters can be determined to generate an initial design for each of the MPSs. The initial design for each MPS can be based on maximizing tissue functionality (for example, in terms of viability and PK-related functions).

Figure 3:
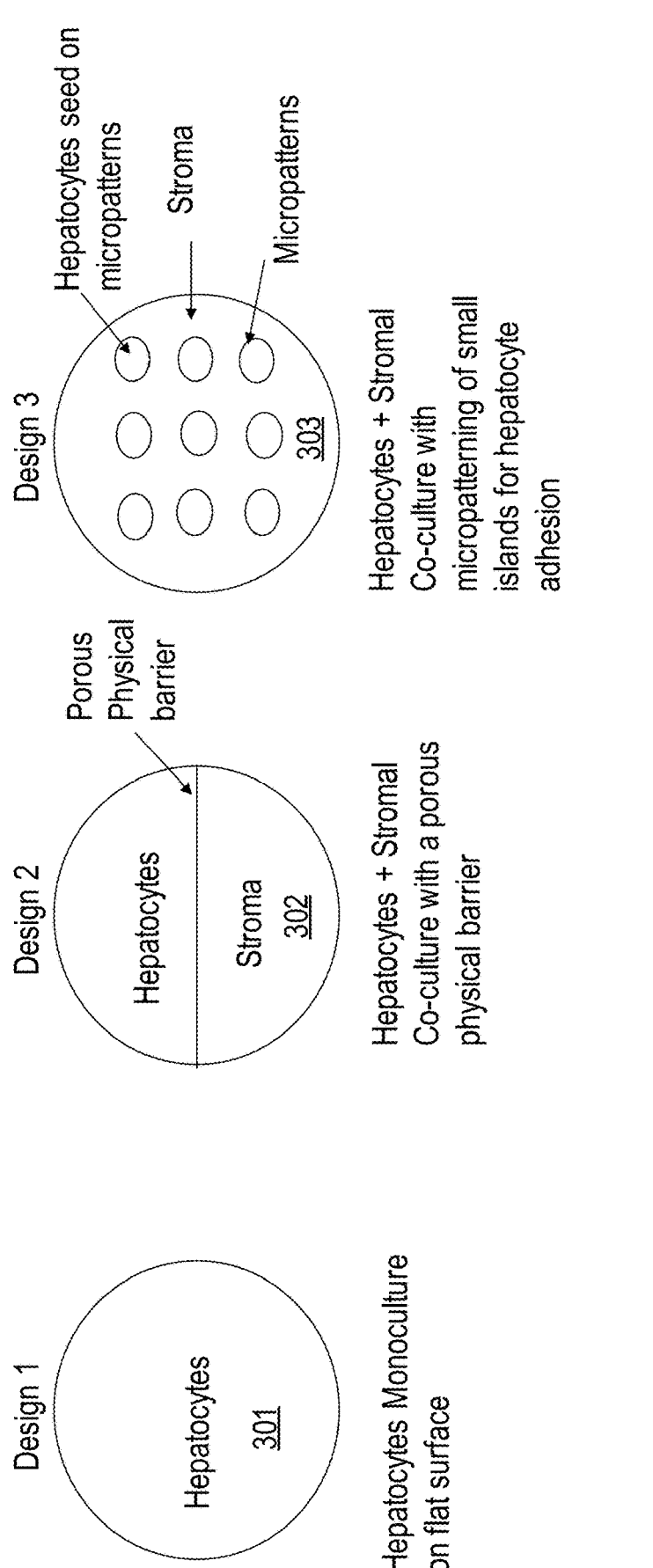
FIG. 3 is a diagram illustrating example designs of MPSes.

FIG. 3 is a diagram illustrating example designs 301-303 of MPSs. In the illustrated implementations, three distinct designs 301-303 of a liver MPS are initially developed, Design 1 (301), Design 2 (302), and Design 3 (303). Design 1 (301) includes a hepatocytes culture (for example, monoculture or co-culture) on a flat surface. Design 2 (302) includes hepatocytes and stromal co-culture with a physical membrane (which can be porous or non-porous) separating the hepatocytes from the stroma. Design 3 (303) includes hepatocytes and stromal co-culture with micro-patterning of small "islands" for hepatocyte adhesion. Example co-culture cell types include hepatocytes, fibroblasts, kupffer, liver, LSECs, and hepatic stellate cells. Several MPS configuration of each design (for example, in terms of cell types, ratio between cell types, and configuration of micropatterns) are experimentally tested and the maximum functionality is determined with respect to PK functionality (for example, the liver MPS having the design/configuration combination resulting in the highest clearance). As used in this specification, a design/configuration combination may be referred to as a pre-design parameter. In some implementations, the predesign parameters resulting in the maximum PK functionality is chosen for use. Examples of PK functionalities that can be used are absorption (for example, for gut MPSs), volume of distribution (for example, for Adipose/skin/muscle MPSs), hepatic clearance (for example, for liver MPS), and excretion (for example, for kidney MPSs).

Referring back to FIG. 2, at block 220, after the initial design of each MPS is chosen, one or more samples are collected of each of the MPSs throughout the predetermined amount of time, and a drug concentration profile is determined for each of the samples.

Figure 4:
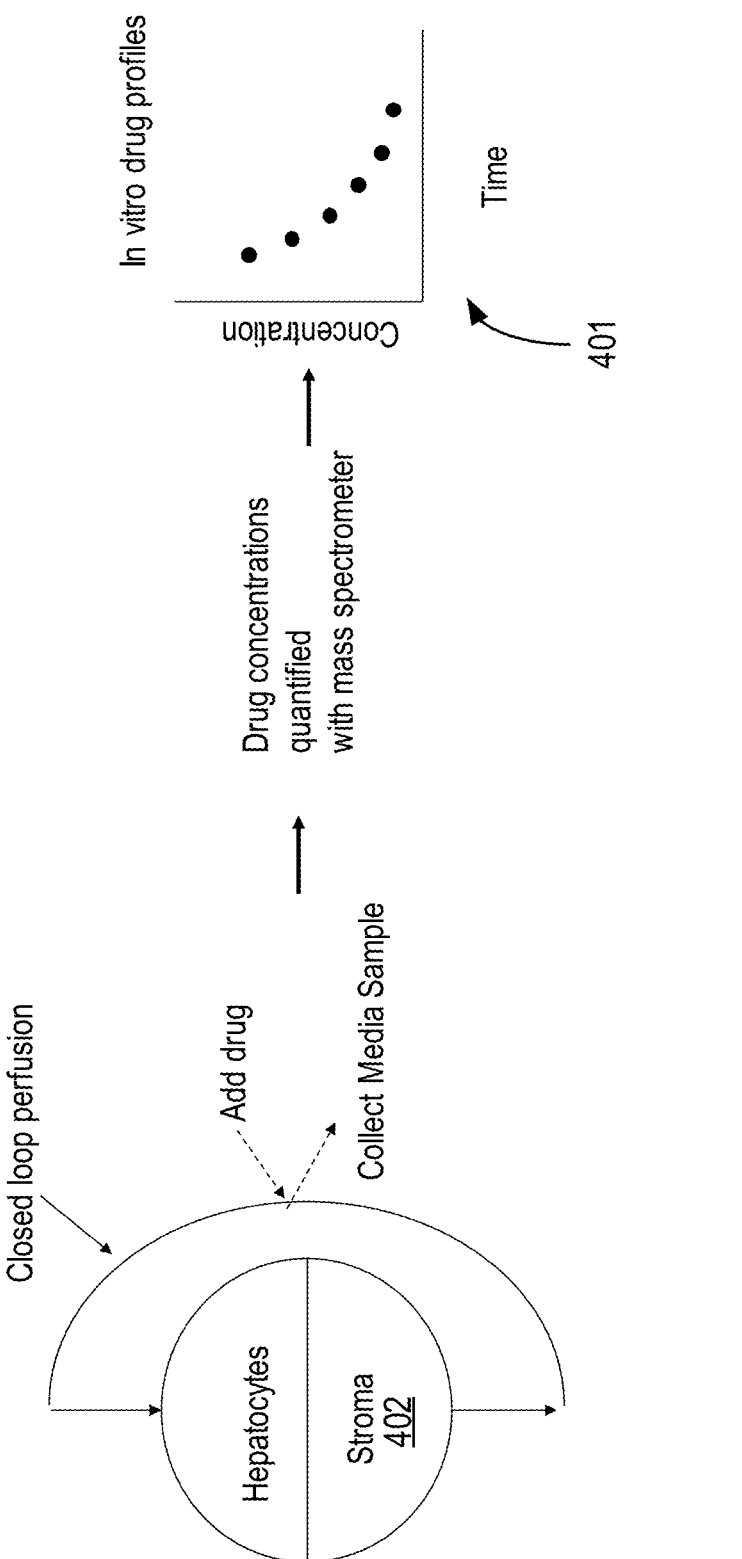
FIG. 4 is a diagram illustrating an example of determining a concentration profile.

FIG. 4 is a diagram illustrating an example of determining a concentration profile 401. In the illustrated implementation, using a closed loop perfusion technique, a drug sample is caused to interact with a liver MPS 402 that was constructed with predesign parameters similar to the Design 2 that was discussed previously with reference to FIG. 3. Samples of the MPS 402 are collected at several time points throughout the predetermined amount of time, and, for each time point, the concentration of the drug is quantified in the sample using mass spectrometry. Based on the quantified concentration of the drug, a concentration profile 401 of the drug is generated.

Referring back to FIG. 2, at block 230, at least one PK parameter is determined based on the concentration profiles. In some implementations, the at least one PK parameter includes at least one PK parameter for each organ type represented by the plurality of MPSs. That is, PK coefficients can be determined independent of the MPS specification (for example, clearance per cell). To determine the PK parameters, first-order differential equations can be used.

Figure 5:
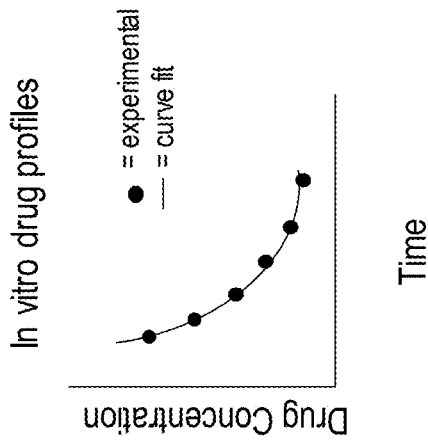
FIG. 5 is a diagram illustrating an example of determining PK parameters

FIG. 5 is a diagram illustrating an example of determining PK parameters. As shown, a first-order differential equation can defined as $$-\frac{d[C]}{dt} = k[C],$$

in which [C] is the drug concentration and k is the elimination rate constant (sometimes referred to as $k_{el}$ in this specification). In some implementations, the first-order differential equation can be used to determine k, which can then be used to determine one or more PK parameters, such as clearance, which can be defined as CL=k/V, where V is the volume of the tested MPS sample. As a result, PK parameters per cell of the MPS can be estimated. For MPSs having basolateral and apical compartments, the following equations can be used:

$$\frac{d[C]_{apical}}{dt} = P * A([C]\text{basal} - [C]\_\text{apical})$$

$$\frac{d[C]_{basal}}{dt} = P * A([C]_{apical} - [C]_{basal})$$

Referring back to FIG. 2, at block 240, the determined PK parameters are used to determine design parameters for the MPS platform. In some implementations, the design parameters include media volume for at least one MPS, surface area for at least one MPS, number of cells for each MPS, media volume for at least one channel, a system level flow rate, a flow pattern, and/or a partitioning of flow. In some implementations, to determine the design parameters, a connectivity diagram is used to derive ordinary differential equations, which can be used, along with the determine PK parameters and known in-human drug kinetic profiles, to optimize the design parameters such that the resulting MPS platform can approximate the known "in human" drug kinetic profiles.

Figure 6:
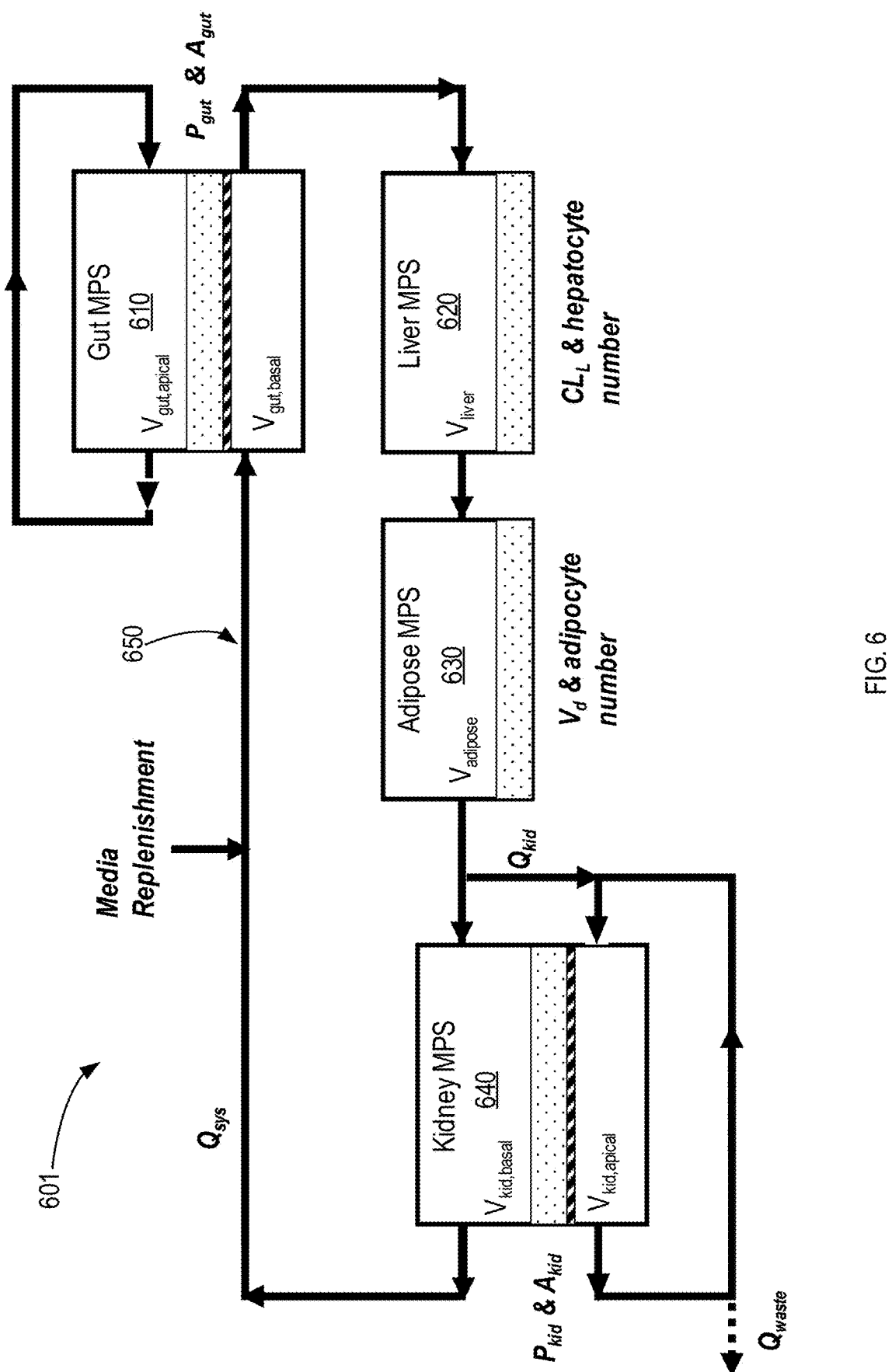
FIG. 6 is a diagram illustrating an example model for determining design parameters.

FIG. 6 is a diagram illustrating an example model 601 for determining design parameters. In the illustrated implementation, a model 601 of a multi-MPS platform is shown, in which the model 601 multi-MPS platform includes a gut MPS 610, a liver MPS 620, an adipose MPS 630, and a kidney MPS 640. The systemic circulation flow rate ($Q_{sys}$) describes the rate of continuous distribution of cell culture medium and drugs among the MPSs. Flow partitioning (that is, the ratio of kidney flowrate ($Q_{kid}$) to systemic flow rate ($Q_{sys}$)) to apical and basolateral compartments of the kidney MPS 640 can be based on physiological ratios of renal blood flow rate (RBF) and glomerulus filtration rate (GFR). Drugs can be administered either to the systemic circulation loop 650 (which can represent intravenous (IV) administration) or the apical compartment of the gut MPS 610 (which can represent oral administration). For the latter, permeability constants ($P_{gut}$) of various drugs for transport through mono-layers of the gut MPS 610, a typical gut epithelium model, can be calculated from drug absorption experiments using an individual gut MPS, derived from either iPS cells or primary gut cells, using computational models based on principles of Fick's law. A drug can be assumed to be metabolized in the liver MPS 620 by hepatocytes. Intrinsic drug clearance rates ($Cl_L$) for parent drugs metabolized by hepatocytes in vitro can be obtained from individual liver MPS experiments using human hepatocytes and computational analysis (for example, applying first order kinetics). A drug can be assumed to be distributed and accumulated on slowly per-fused organs, such as adipose, muscle or skin tissues. Volume of distribution ($V_d$) parameters can be estimated from the experiments using the adipose MPS 630. Drugs which undergo glomerular filtration translocate in the kidney lumen and then reabsorb into the systemic circulation. Additionally, drugs in the systemic circulation are secreted from the blood stream to the lumen of nephrons. The permeability rate constants ($P_{kid}$) for reabsorption and secre-tion can be estimated in individual kidney MPS experiments and analyzed with computational models based on Fick's law. Drugs which enter to the lumen of the kidney, but are not fully reabsorbed to systemic recirculation, are typically excreted in urine. To recapitulate excretion of a parent drug from the kidney MPS, a constant flow to a waste container ($Q_{waste}$) can be introduced and set equal to the renal luminal flow ($Q_{kid}$). As no active filtration between medium and drug may occur, the medium can be replenished at the same rate as the excretion rate ($Q_{waste}$) to the basal circulation (media replenishment).

Mechanistic computational models can be implemented to describe absorption, distribution, metabolism, and excre-tion processes using conservation of mass principles with ordinary differential equations for each of the platforms. These models can be used to convert experimental drug kinetic data from individual MPSs into pharmacokinetic parameters such as $Cl_L$, $P_{kid}$, $P_{gut}$ and $V_d$. A multi-functional scaling technique can further be used to inform the design parameters of the interconnected MPS platform (for example, surface areas for gut and kidney MPSs ($A_{gut}$ and $A_{kidney}$, respectively) and cell numbers for liver and adipose MPSs). The multi-functional scaling technique can include an objective function that is a weighted squared difference between a model outcome and corresponding measurements as defined by $$\text{Objective Function} = \left(\frac{\text{prediction} - \text{observation}}{\text{prediction}}\right)^2$$

in which the prediction describes the model outcome and the observation corresponds to clinical data for the study objec-tive. The design parameters can be estimated by computa-tionally minimizing the objective function.

In the illustrated implementation, the objective includes two elements: (i) recapitulating clinically observed plasma concentration profiles (observation) of each drug of a train-ing set and (ii) in the multi-MPS platform using model calculations of the drug concentration profiles (prediction) in the systemic circulation. In vitro PK parameters ($Cl_L$, $P_{kid}$, $P_{gut}$ and $V_d$) obtained from individual MPS experiments are implemented as fixed parameters into the multi-functional scaling model along with the design parameters of the multi-MPS platform ($A_{gut}$, $A_{kidney}$, number of hepatocytes and adipocytes), which can be estimated by minimizing the objective function. Training sets of drugs can simultane-ously contain several drug time concentration profiles to be used in the computations. To account for the dose and bioavailability differences of drugs in vivo (observation), the in vivo time concentration profiles can be normalized as follows:

$$c(t)'_{invivo} = c(t)_{invivo} \times \frac{v}{F \times D} \quad (1)$$

where $c(t)_{invivo}$ is the measured time-dependent drug plasma concentration, $c(t)_{invivo'}$ is the normalized drug concentration, F is bioavailability, D is the adminis-tered dose, Vis the volume of distribution, and t is time.

For the computational simulations (prediction), a normal-ized drug concentration can be administered to the platform (e.g unit concentration of 1 μg ml$^{-1}$), which can be equiva-lent to an administered dose of 1 μg for an apical volume of the gut MPS of 1 ml. To compare the in vitro platform response to the normalized in vivo time concentration pro-files, the same conceptual normalization can be performed for the model concentration:

$$c(t)'_{in} = c(t)_{in} \times \frac{V_{invitro}}{F_{invitro} \times D_{invitro}} \quad (3)$$

where $V_{invitro}$ is the total media volume of the platform, $D_{invitro}$ is the administered dose to the apical site of the gut-MPS ("oral dose") and $F_{invitro}$ is the fraction of drug in the systemic circulation. This normalization method for both the in vivo and in vitro time-concen-tration profiles can allow simultaneous comparison of various drugs at the same unit concentration, although administered at different doses in human. The normal-ized concentration differences then can be directly compared in the objective function.

In the illustrated implementation, the following design parameters can be investigated: the gut, liver, adipose and kidney MPS compartment volumes, the gut and kidney MPS surface areas, the liver and adipose MPS cell numbers, systemic flow rate ($Q_{sys}$) and MPS-specific flow rate (for example, $Q_{kid}$). To reduce the number of fitting parameters, the apical compartment volumes can be fixed based on practical considerations, such as nutrient requirements of tissue culture obtained from previous experimental results. Prior to parameter optimization algorithms, certain limits on the range of design parameters to be fitted can be imposed based on, for example, experimental feasibility and practicality. In the illustrated implementation, allowable ranges for medium volumes of total system include 0.1-5 ml, and for the filtered flow to the kidney, the allowable range includes 1-10 ml per day.

Referring back to FIG. 2, at block 250, the design parameters are combined with the predesign parameters for each MPS to construct the MPS platform. Once constructed, the MPS platform can be validated by comparing the prediction resulting from block 240 to experimental results using the multi-MPS platform. If the results are within a threshold, the MPS can be validated for use. If the results are not within the threshold, blocks 240-250 can be repeated as necessary.

Figure 7:
FIG. 7 is a flow chart illustrating an example method of performing a PK study using a multi-MPS platform.
Figure 7:
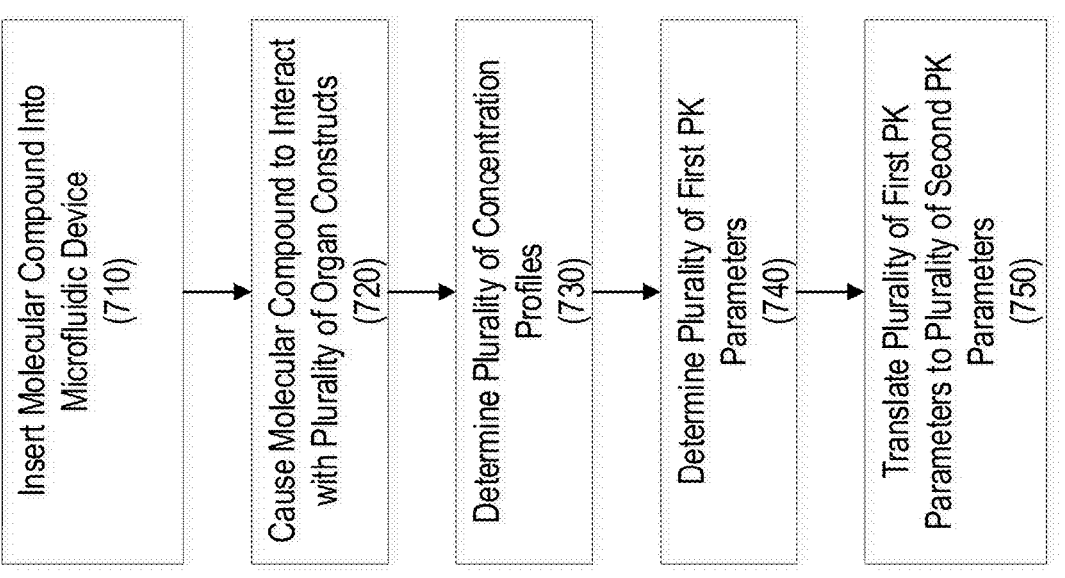

FIG. 7 is a flow chart illustrating an example method 700 of performing a PK study using a multi-MPS platform. The method includes inserting a molecular compound into a microfluidic device (block 710), causing the molecular compound to interact with a plurality of organ constructs (block 720), determining a plurality of concentration profiles (block 730), determining a plurality of first PK parameters (block 740), and translating the plurality of first PK parameters to a plurality of second PK parameters (block 750).

At block 710, a molecular compound (for example, a drug sample) is inserted in a microfluidic device, such as the MPS platform 100 described previously with reference to FIG. 1. The microfluidic device can include a plurality of organ constructs. In some implementations, the microfluidic device includes four or more organ constructs. The plurality of organ constructs can include a liver organ construct, a kidney organ construct, a muscle organ construct, and/or an adipose organ construct. At least one of the plurality of organ constructs can comprise an apical membrane, a basolateral membrane, or both.

At block 720, the molecular compound is caused to flow through the microfluidic device such that it interacts with the organ constructs (for example, MPSs) of the microfluidic device. In some implementations, this includes causing distribution of the molecular compound at a circulation flow rate at which the molecular compound is distributed at a threshold distribution rate. The threshold distribution rate can be determined using the method 200 discussed previously with reference to FIG. 2 (for example, when determining the design parameters of the MPS platform).

At block 730, at one or more time points during a period of time that the molecular compound is caused to flow through the microfluidic device, samples are taken from each molecular construct to determine a concentration profile for each of the molecular constructs. In some implementations, mass spectrometry is performed on the samples to determine the concentration profile.

At block 740, a plurality of in vitro PK parameters are determined for the microfluidic device based on the concentration profiles, as described previously with reference to FIG. 2. The plurality of in vitro PK parameters can include clearance, absorption, volume of distribution, and excretion. As indicated previously, the in vitro PK parameters can be independent of the specifications of the organ constructs. At least one ordinary differential equation can be used to determine the in vitro PK parameters using the concentration profiles.

At block 750, the in vitro PK parameters are used to determine in vivo PK parameters. In some implementations, a physiologically based pharmacokinetic (PBPK) and/or quantitative systems pharmacology (QSP) model is used to translate the in vitro PK parameters to the in vivo PK parameters. A QSP model can be developed based on an array of biological and (patho)physiological data as well as information about target and drug characteristics (for example, human pathophysiology, biochemistry, cell biology, genomics, in vivo data, clinical data, target characteristics, drug characteristics, pharmacology, and so forth). Then, quantitative information derived from MPS experimentation provides values or ranges of specific parameters to the QSP models. MPS results might relate specifically to drug activity or might provide biology-specific parameters with which to define virtual patient biology for simulations of drug activity derived from other sources. In some implementations, the QSP/PBPK models can include a scaling factor to scale the in vitro PK parameters to the in vivo PK paramters. For example, because a liver MPS may only include 100,000 liver cells, while an average human liver may include 3,000,000,000 liver cells, it may be beneficial to scale the in vitro parameters to the human specifications. In some implementations, one or more machine learning models is used to determine an empirical scaling factor (ESF) to scale the in vitro parameters to the in vivo parameters. As will be described later, the ESF can be determined by the machine learning model using the molecular structure of the drug used in the experiments based on known outcomes of previous experiments using drugs of similar molecular structure.

Figure 8:
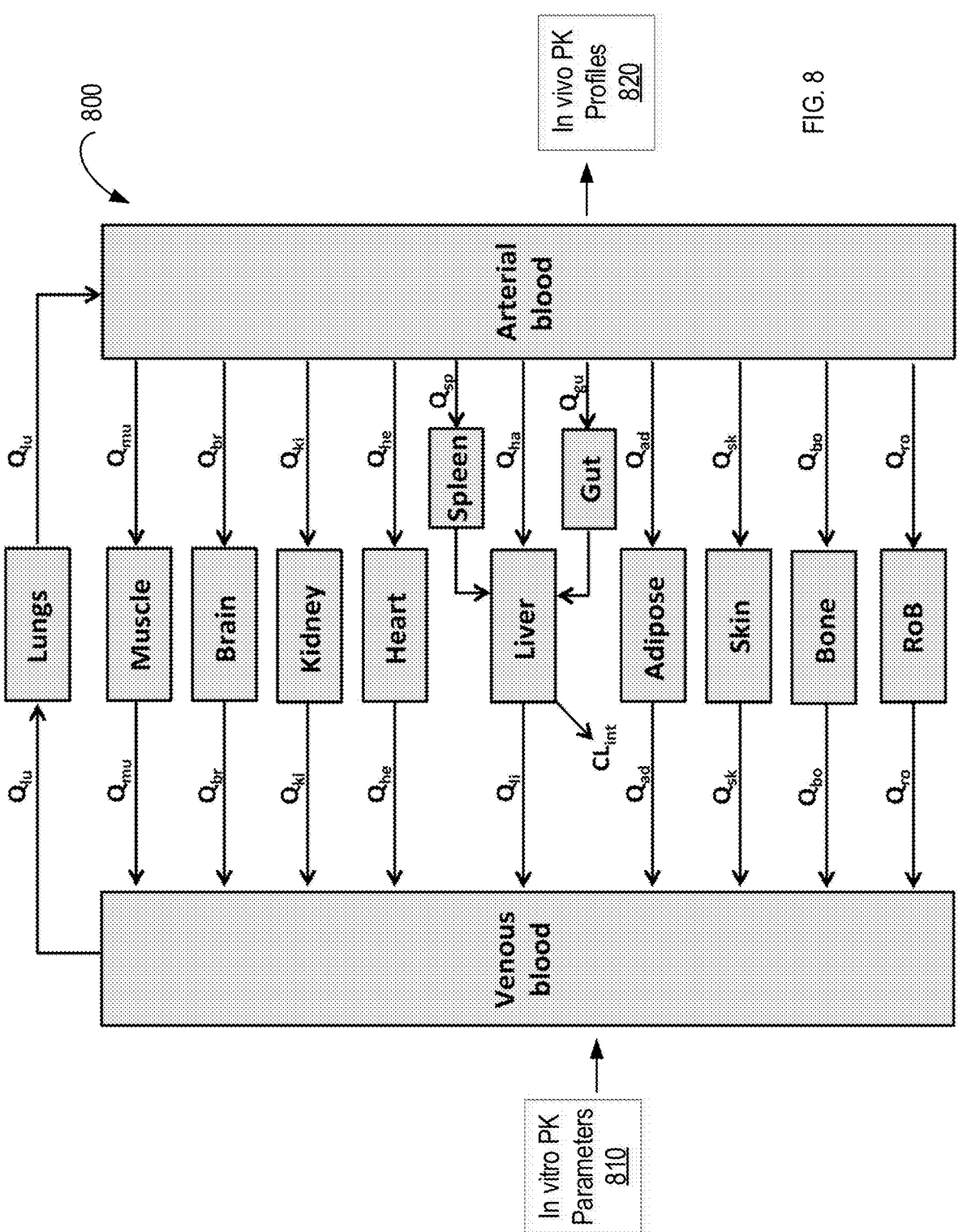
FIG. 8 is a flow chart illustrating an example model for translating in vitro PK parameters to in vivo PK parameters.

FIG. 8 is a flow chart illustrating an example model 800 for translating in vitro PK parameters to in vivo PK parameters. The human physiologically based pharmacokinetic (PBPK) model 800 illustrated in FIG. 8, which can be based on conservation of mass principles, can be used to translate in vitro PK results to human in vivo profiles. In the illustrated implementation, the PK parameters obtained from the in vitro MPSs (for example, liver MPS, kidney MPS, adipose MPS, gut MPS, and so forth) can be used as input parameters 810 in corresponding components of the human PBPK model 800. That is, intrinsic clearance values, for example, can be obtained from a liver MPS of the MPS platform and used as input parameters for the liver component of the PBPK model 800. The parameters can be adjusted based on the differences between in vitro and in vivo physiology (such as cell numbers and enzymatic activity differences), and drug specific parameters (such as physiochemical properties). For physiological differences, the parameters can be directly scaled. For example, scaling can be based on the number of liver cells of the liver MPS and number of liver cells in the human liver. For drug specific parameters, empirical scaling factors (ESFs) can be used. ESF parameters for new molecular entities can be estimated using machine learning algorithms, as described later. The scaled in vitro parameters can then be used in the PBPK model 800 to translate the in vitro MPS results to in vivo human PK profiles 820. This approach can be applied for several PK parameters, such as permeability parameters in gut and kidney, hepatic clearance in liver, volume of distribution in adipose, and so on.

Figure 9:
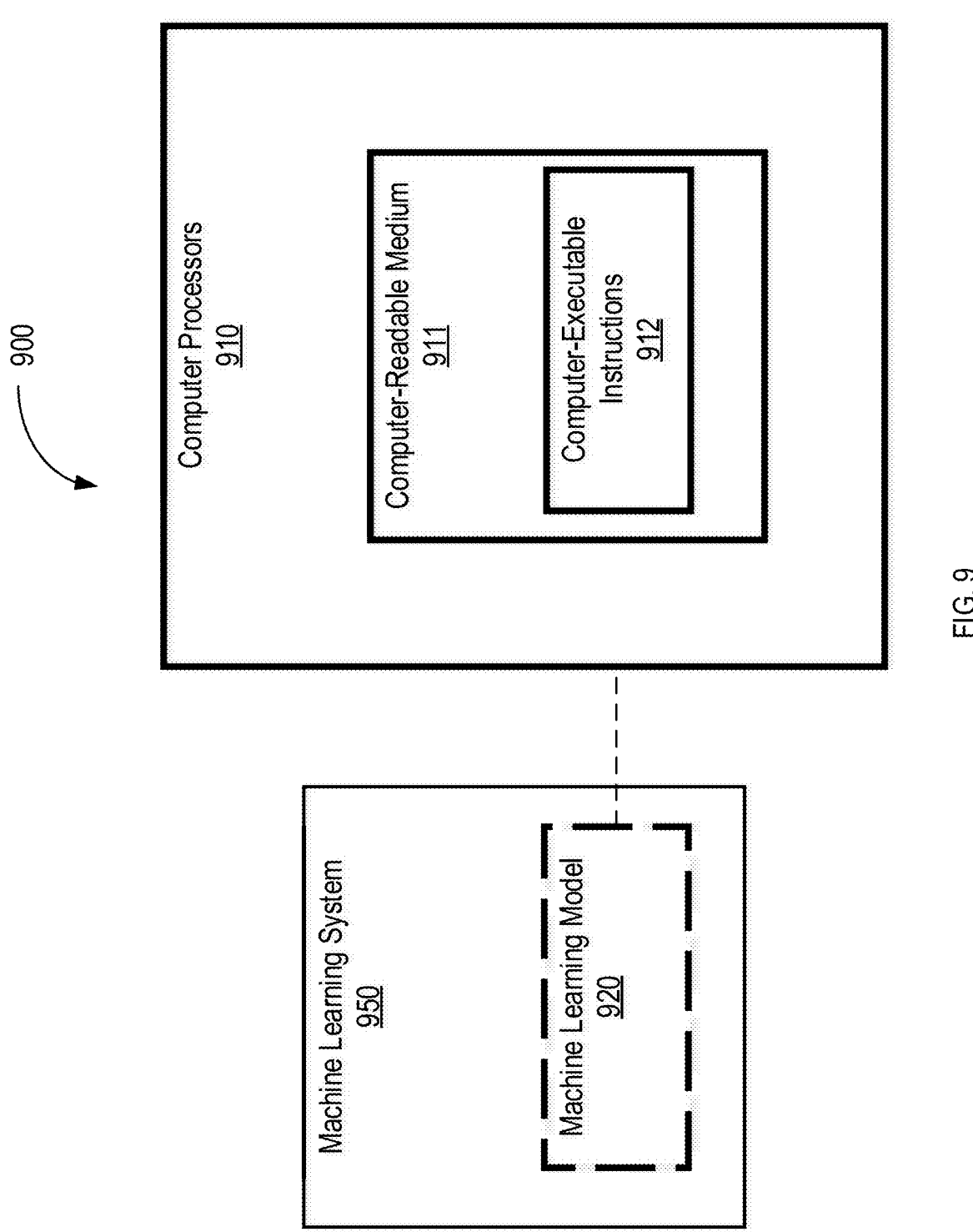
FIG. 9 is a diagram illustrating an example computer system configured to execute a machine learning model.

FIG. 9 is a diagram illustrating an example computer system 900 configured to execute a machine learning model. Generally, the computer system 900 is configured to process data indicating a molecular structure and determine an ESF for scaling in vitro PK parameters to in vivo PK parameters. The system 900 includes computer processors 910. The computer processors 910 include computer-readable memory 911 and computer readable instructions 912. The system 900 also includes a machine learning system 950. The machine learning system 950 includes a machine learning model 920. The machine learning model 920 can be separate from or integrated with the computer processors 910.

The computer-readable medium 911 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In an embodiment, the computer-readable medium 911 includes code-segment having executable instructions.

In some implementations, the computer processors 910 include a general purpose processor. In some implementations, the computer processors 910 include a central processing unit (CPU). In some implementations, the computer processors 910 include at least one application specific integrated circuit (ASIC). The computer processors 910 can also include general purpose programmable microprocessors, graphic processing units, special-purpose programmable microprocessors, digital signal processors (DSPs), programmable logic arrays (PLAs), field programmable gate arrays (FPGA), special purpose electronic circuits, etc., or a combination thereof. The computer processors 910 are configured to execute program code means such as the computer-executable instructions 912 and configured to execute executable logic that includes the machine learning model 920.

The computer processors 910 are configured to receive data indicating a molecular structure of, for example, a drug. The data can be obtained through one or more means, such as wireless communications with databases, optical fiber communications, USB, CD-ROM, and so forth.

The machine learning model 920 is capable of processing the data to determine an ESF. In some implementations, the machine learning model 920 is trained to determine ESF using a data set that includes molecular properties (for example, chemical structure and/or physiochemical properties) of several drugs, the in vitro PK parameters of the drugs determined using an MPS platform, and known human in vivo PK parameters of the drugs. The machine learning model 920 can determine a scaling factor between the in vivo PK parameters and the in vitro PK parameters for each drug, and associate the scaling factor with the molecular properties of the drug. Accordingly, when a new drug is introduced to the machine learning model 920, it can determine a scaling factor for the in vitro PK properties of the drug that were obtained using the MPS platform based on the molecular properties of the drug.

The machine learning system 950 is capable of applying machine learning techniques to train the machine learning model 920. As part of the training of the machine learning model 920, the machine learning system 950 forms a training set of input data by identifying a positive training set of input data items that have been determined to have the property in question, and, in some embodiments, forms a negative training set of input data items that lack the property in question.

The machine learning system 950 extracts feature values from the input data of the training set, the features being variables deemed potentially relevant to whether or not the input data items have the associated property or properties. An ordered list of the features for the input data is herein referred to as the feature vector for the input data. In one embodiment, the machine learning system 950 applies dimensionality reduction (e.g., via linear discriminant analysis (LDA), principle component analysis (PCA), or the like) to reduce the amount of data in the feature vectors for the input data to a smaller, more representative set of data.

In some implementations, the machine learning system 950 uses supervised machine learning to train the machine learning models 920 with the feature vectors of the positive training set and the negative training set serving as the inputs. Different machine learning techniques-such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different embodiments. The machine learning model 920, when applied to the feature vector extracted from the input data item, outputs an indication of whether the input data item has the property in question, such as a Boolean yes/no estimate, or a scalar value representing a probability.

In some embodiments, a validation set is formed of additional input data, other than those in the training sets, which have already been determined to have or to lack the property in question. The machine learning system 950 applies the trained machine learning model 920 to the data of the validation set to quantify the accuracy of the machine learning model 920. Common metrics applied in accuracy measurement include: Precision=TP/(TP+FP) and Recall=TP/(TP+FN), where precision is how many the machine learning model correctly predicted (TP or true positives) out of the total it predicted (TP+FP or false positives), and recall is how many the machine learning model correctly predicted (TP) out of the total number of input data items that did have the property in question (TP+FN or false negatives). The F score (F-score=2*PR/(P+R)) unifies precision and recall into a single measure. In one embodiment, the machine learning module iteratively re-trains the machine learning model until the occurrence of a stopping condition, such as the accuracy measurement indication that the model is sufficiently accurate, or a number of training rounds having taken place.

In some implementations, the machine learning model 920 is a convolutional neural network (CNN). A CNN can be configured based on a presumption that inputs to the CNN correspond to image pixel data for an image or other data that includes features at multiple spatial locations. For example, sets of inputs can form a multi-dimensional data structure, such as a tensor, that represent color features of an example digital image (e.g., a biological image of biological tissue). In some implementations, inputs to the CNN correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the CNN can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which CNN performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R,G,B. A convolutional layer of a CNN of the machine learning model 920 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the machine learning model 920 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The machine learning model 920 can then compute a dot product from the overlapped elements. For example, the machine learning model 920 can convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The machine learning model 920 can convolve each kernel over each input of an input volume. The machine learning model 920 can perform this convolution operation by, for example, moving (or sliding) each kernel over each input in the region.

The machine learning model 920 can move each kernel over inputs of the region based on a stride value for a given convolutional layer. For example, when the stride is set to 1, then the machine learning model 920 can move the kernels over the region one pixel (or input) at a time. Likewise, when the stride is 2, then the machine learning model 920 can move the kernels over the region two pixels at a time. Thus, kernels may be shifted based on a stride value for a layer and the machine learning model 920 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the machine learning model 920 can produce a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the CNN.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In some implementations, the spatial size of the output volume is computed as a function of the input volume size, W, using the formula $(W-F+2P)/S+1$. For example, an input tensor can represent a pixel input volume of size [227×227×3]. A convolutional layer of a CNN can have a spatial extent value of F=11, a stride value of S=4, and no zero-padding (P=0). Using the above formula and a layer kernel quantity of K=96, the machine learning model 920 performs computations for the layer that results in a convolutional layer output volume of size [55×55×96], where 55 is obtained from [(227-11+0)/4+1=55].

The computations (e.g., dot product computations) for a convolutional layer, or other layers, of a CNN involve performing mathematical operations, e.g., multiplication and addition, using a computation unit of a hardware circuit of the machine learning model 920. The design of a hardware circuit can cause a system to be limited in its ability to fully utilize computing cells of the circuit when performing computations for layers of a neural network.

Figure 10:
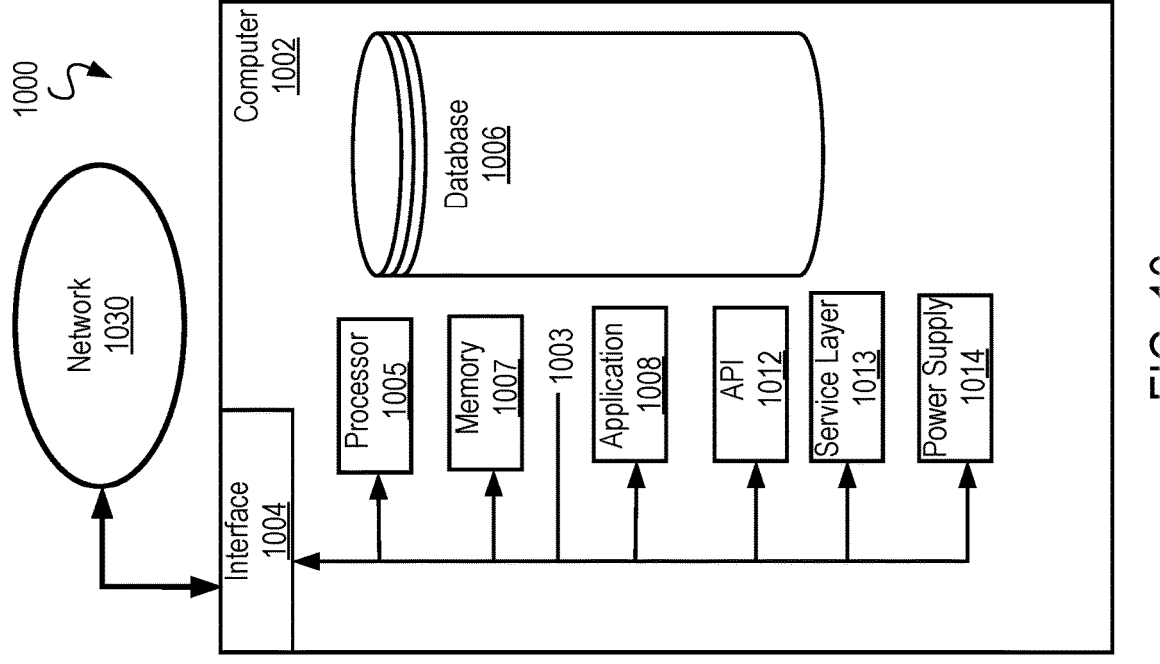
FIG. 10 is a block diagram of an example computer system used to provide computational functionalities associated with described algorithms, methods, functions, processes, flows, and procedures described in the present disclosure

FIG. 10 is a block diagram of an example computer system 1000 used to provide computational functionalities associated with described algorithms, methods, functions, processes, flows, and procedures described in the present disclosure (such as the method 200 described previously with reference to FIG. 2), according to some implementations of the present disclosure. The illustrated computer 1002 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1002 can include input devices such as keypads, keyboards, and touch screens that can accept user information. Also, the computer 1002 can include output devices that can convey information associated with the operation of the computer 1002. The information can include digital data, visual data, audio information, or a combination of information. The information can be presented in a graphical user interface (UI or GUI).

The computer 1002 can serve in a role as a client, a network component, a server, a database, a persistency, or components of a computer system for performing the subject matter described in the present disclosure. The illustrated computer 1002 is communicably coupled with a network 1030. In some implementations, one or more components of the computer 1002 can be configured to operate within different environments, including cloud-computing-based environments, local environments, global environments, and combinations of environments.

At a high level, the computer 1002 is an electronic computing device operable to receive, transmit, process, store, and manage data and information associated with the described subject matter. According to some implementations, the computer 1002 can also include, or be communicably coupled with, an application server, an email server, a web server, a caching server, a streaming data server, or a combination of servers.

The computer 1002 can receive requests over network 1030 from a client application (for example, executing on another computer 1002). The computer 1002 can respond to the received requests by processing the received requests using software applications. Requests can also be sent to the computer 1002 from internal users (for example, from a command console), external (or third) parties, automated applications, entities, individuals, systems, and computers.

Each of the components of the computer 1002 can communicate using a system bus 1003. In some implementations, any or all of the components of the computer 1002, including hardware or software components, can interface with each other or the interface 1004 (or a combination of both), over the system bus 1003. Interfaces can use an application programming interface (API) 1012, a service layer 1013, or a combination of the API 1012 and service layer 1013. The API 1012 can include specifications for routines, data structures, and object classes. The API 1012 can be either computer-language independent or dependent. The API 1012 can refer to a complete interface, a single function, or a set of APIs.

The service layer 1013 can provide software services to the computer 1002 and other components (whether illustrated or not) that are communicably coupled to the computer 1002. The functionality of the computer 1002 can be accessible for all service consumers using this service layer. Software services, such as those provided by the service layer 1013, can provide reusable, defined functionalities through a defined interface. For example, the interface can be software written in JAVA, C++, or a language providing data in extensible markup language (XML) format. While illustrated as an integrated component of the computer 1002, in alternative implementations, the API 1012 or the service layer 1013 can be stand-alone components in relation to other components of the computer 1002 and other components communicably coupled to the computer 1002. Moreover, any or all parts of the API 1012 or the service layer 1013 can be implemented as child or sub-modules of another software module, enterprise application, or hardware module without departing from the scope of the present disclosure.

The computer 1002 includes an interface 1004. Although illustrated as a single interface 1004 in FIG. 10, two or more interfaces 1004 can be used according to particular needs, desires, or particular implementations of the computer 1002 and the described functionality. The interface 1004 can be used by the computer 1002 for communicating with other systems that are connected to the network 1030 (whether illustrated or not) in a distributed environment. Generally, the interface 1004 can include, or be implemented using, logic encoded in software or hardware (or a combination of software and hardware) operable to communicate with the network 1030. More specifically, the interface 1004 can include software supporting one or more communication protocols associated with communications. As such, the network 1030 or the interface's hardware can be operable to communicate physical signals within and outside of the illustrated computer 1002.

The computer 1002 includes a processor 1005. Although illustrated as a single processor 1005 in FIG. 10, two or more processors 1005 can be used according to particular needs, desires, or particular implementations of the computer 1002 and the described functionality. Generally, the processor 1005 can execute instructions and can manipulate data to perform the operations of the computer 1002, including operations using algorithms, methods, functions, processes, flows, and procedures as described in the present disclosure.

The computer 1002 also includes a database 1006 that can hold data for the computer 1002 and other components connected to the network 1030 (whether illustrated or not). For example, database 1006 can be an in-memory, conventional, or a database storing data consistent with the present disclosure. In some implementations, database 1006 can be a combination of two or more different database types (for example, hybrid in-memory and conventional databases) according to particular needs, desires, or particular implementations of the computer 1002 and the described functionality. Although illustrated as a single database 1006 in FIG. 10, two or more databases (of the same, different, or combination of types) can be used according to particular needs, desires, or particular implementations of the computer 1002 and the described functionality. While database 1006 is illustrated as an internal component of the computer 1002, in alternative implementations, database 1006 can be external to the computer 1002.

The computer 1002 also includes a memory 1007 that can hold data for the computer 1002 or a combination of components connected to the network 1030 (whether illustrated or not). Memory 1007 can store any data consistent with the present disclosure. In some implementations, memory 1007 can be a combination of two or more different types of memory (for example, a combination of semiconductor and magnetic storage) according to particular needs, desires, or particular implementations of the computer 1002 and the described functionality. Although illustrated as a single memory 1007 in FIG. 10, two or more memories 1007 (of the same, different, or combination of types) can be used according to particular needs, desires, or particular implementations of the computer 1002 and the described functionality. While memory 1007 is illustrated as an internal component of the computer 1002, in alternative implementations, memory 1007 can be external to the computer 1002.

The application 1008 can be an algorithmic software engine providing functionality according to particular needs, desires, or particular implementations of the computer 1002 and the described functionality. For example, application 1008 can serve as one or more components, modules, or applications. Further, although illustrated as a single application 1008, the application 1008 can be implemented as multiple applications 1008 on the computer 1002. In addition, although illustrated as internal to the computer 1002, in alternative implementations, the application 1008 can be external to the computer 1002.

The computer 1002 can also include a power supply 1014. The power supply 1014 can include a rechargeable or non-rechargeable battery that can be configured to be either user- or non-user-replaceable. In some implementations, the power supply 1014 can include power-conversion and management circuits, including recharging, standby, and power management functionalities. In some implementations, the power-supply 1014 can include a power plug to allow the computer 1002 to be plugged into a wall socket or a power source to, for example, power the computer 1002 or recharge a rechargeable battery.

There can be any number of computers 1002 associated with, or external to, a computer system containing computer 1002, with each computer 1002 communicating over network 1030. Further, the terms "client," "user," and other appropriate terminology can be used interchangeably, as appropriate, without departing from the scope of the present disclosure. Moreover, the present disclosure contemplates that many users can use one computer 1002 and one user can use multiple computers 1002.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX®, UNIX®, WINDOWS®, MAC OS™, ANDROID™, or IOS™.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising" or "further including" in the foregoing description or following claims, what follows this phrase can be an additional step or entity, or a sub-step/sub-entity of a previously-recited step or entity.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure.

What is claimed is:

1. A method, comprising:

receiving a molecular compound in a microfluidic device comprising a plurality of organ constructs and a fluid loop configured to recirculate a fluid media through the plurality of organ constructs;

recirculating the molecular compound through the microfluidic device at a specified flow rate to cause the molecular compound to interact with the plurality of organ constructs, the flow rate based on a type of at least one of the organ constructs;

measuring one or more concentration values of the molecular compound at one or more of the organ constructs based on the interacting;

determining, by a computing device associated with the microfluidic device, based at least partially on the measuring, a plurality of concentration profiles for the molecular compound, each concentration profile of the plurality being associated with a respective organ construct of the microfluidic device;

determining, by the computing device and based at least partially on the plurality of concentration profiles, a plurality of first pharmacokinetic (PK) parameters comprising a first type;

translating, by the computing device and based on the type of at least one of the organ constructs, the plurality of first PK parameters to a plurality of second PK parameters comprising a second type, the translating comprising executing a quantitative systems pharmacology (QSP) model that includes an empirical scaling factor (ESF) to scale in vitro parameters to in vivo parameters, the ESF being determined based on a machine learning model trained with a data set representing molecular properties of molecular compounds, the molecular properties including a chemical structure or physiochemical properties of the molecular compounds, in vitro PK parameter profiles corresponding to the molecular compounds in the microfluidic device, and in vivo PK parameter profiles of the molecular compounds, and wherein the machine learning model is selected based on known outcomes of previous circulations in the microfluidic device of a molecular compound of a similar molecular structure;

generating, by the computing device, data comprising a profile comprising the second PK parameters, the profile comprising PK parameters simulating in vivo data; and outputting, by the computing device, the generated data comprising the profile to a data store.

2. The method of claim 1, wherein flowing the molecular compound through the microfluidic device comprises causing distribution of the molecular compound at a circulation flow rate at which the molecular compound is distributed as a threshold distribution rate.

3. The method of claim 1, wherein the plurality of organ constructs comprises at least four organ constructs.

4. The method of claim 1, wherein the plurality of organ constructs comprises at least one of: a gastrointestinal tract organ construct, a liver organ construct, a kidney organ construct, a muscle organ construct, or an adipose organ construct.

5. The method of claim 1, wherein at least one organ construct of the plurality of organ constructs comprises an apical compartment and a basolateral compartment, the apical compartment associated with a first fluid loop, and the basolateral compartment associated with a second fluid loop.

6. The method of claim 1, wherein each of the plurality of organ constructs comprises at least one of: an apical compartment or a basolateral compartment.

7. The method of claim 1, wherein a pharmacokinetic parameter comprises a clearance, a permeability, or a volume of distribution.

8. The method of claim 1, wherein determining at least one pharmacokinetic parameter comprises using at least one ordinary differential equation.

9. The method of claim 1, wherein the first type of PK parameters comprises in vitro PK parameters and the second type of PK parameters comprises human PK parameters.

10. The method of claim 1, wherein a first organ construct of the plurality of organ constructs is associated with a first input fluidic channel that causes a first flow rate, and wherein a second organ construct of the plurality of organ constructs is associated with a second an input fluidic channel that causes a second flow rate that is different than the first flow rate.

11. The method of claim 1, wherein at least one organ construct of the plurality of organ constructs comprises an apical compartment and a basolateral compartment, the apical compartment associated with non-circulatory fluid loop that does not recirculate the fluid media, and the basolateral compartment associated with a second fluid loop that recirculates the fluid media.

12. The method of claim 1, further comprising:
controlling recirculation of the molecular compound through the microfluidic device at the specified flow rate to cause a predefined level of shear stress of the fluid media on tissue in at least one organ construct of the plurality of organ constructs.

13. The method of claim 1, wherein controlling recirculation of the molecular compound through the microfluidic device at the specified flow rate to cause the molecular compound to interact with the plurality of organ constructs comprises a closed loop perfusion of the fluid media through tissue of at least one organ construct of the plurality of organ constructs.

14. The method of claim 1, wherein translating, based on the type of at least one of the organ constructs, the plurality of first PK parameters to a plurality of second PK parameters comprising a second type comprises executing a machine learning model that is selected based on the type of at least one of the organ constructs.

15. The method of claim 1 wherein translating, based on the type of at least one of the organ constructs, the plurality of first PK parameters to a plurality of second PK parameters comprising a second type comprises scaling values of the first PK parameters based on the type of at least one of the organ constructs.

16. The method of claim 1, further comprising:
training the machine learning model for a value of an empirical scaling factor for translating the plurality of first PK parameters to the plurality of second PK parameters comprising the second type,
wherein the first type includes in vitro PK results, and the second type includes in vivo profiles, the training based on a data set that includes molecular properties of molecular compounds,
wherein the molecular properties include a chemical structure or physiochemical properties of the molecular compounds, in vitro PK parameters of the molecular compounds, or in vivo PK parameters value of the molecular compounds.

17. The method of claim 1, further comprising determining a drug dosage regimen for a drug based on the generated data comprising the profile.

* * * * *